United States Patent
Wofford et al.

(10) Patent No.: US 6,683,280 B1
(45) Date of Patent: Jan. 27, 2004

(54) APPARATUS AND METHOD FOR PROSTHESIS SECUREMENT

(76) Inventors: Jeffrey S. Wofford, 1944 Chiswick Rd., Knoxville, TN (US) 37922; James R. Lawson, Jr., 1418 Willowbrooke Cir., Franklin, TN (US) 37069; Patrick B. Gerard, 5604 Chapman Hwy., Knoxville, TN (US) 37920

( * ) Notice: Subject to any disclaimer, the term of this patent is extended or adjusted under 35 U.S.C. 154(b) by 0 days.

(21) Appl. No.: 10/386,846

(22) Filed: Mar. 12, 2003

(51) Int. Cl.[7] .............................. H05B 1/00; A61B 17/58
(52) U.S. Cl. ............................ 219/233; 606/92; 606/29; 606/30; 607/108
(58) Field of Search ................................ 219/233, 217, 219/212, 524, 527, 211; 607/108, 3, 96; 606/92, 29, 30

(56) References Cited

U.S. PATENT DOCUMENTS

| | | | |
|---|---|---|---|
| 3,634,655 A | * 1/1972 | Jordan | 219/527 |
| 3,796,855 A | * 3/1974 | Brown et al. | 219/211 |
| 3,919,723 A | 11/1975 | Heimke et al. | |
| 4,409,662 A | * 10/1983 | Rao | 700/300 |
| 4,702,236 A | 10/1987 | Tarabichy et al. | |
| 4,769,400 A | 9/1988 | Geist et al. | |
| 4,873,969 A | 10/1989 | Huebsch | |
| 4,910,386 A | 3/1990 | Johnson | |
| 5,019,083 A | 5/1991 | Klapper et al. | |
| 5,037,437 A | * 8/1991 | Matsen, III | 128/898 |
| 5,132,518 A | 7/1992 | Solacoff | |
| 5,151,099 A | 9/1992 | Young et al. | |
| 5,163,933 A | 11/1992 | Grundfest | |
| 5,462,552 A | * 10/1995 | Kiester | 606/92 |
| 5,468,245 A | 11/1995 | Vargas, III | |
| 5,549,705 A | * 8/1996 | Michielli et al. | 623/23.37 |
| 5,679,299 A | 10/1997 | Gilbert et al. | |
| 5,736,038 A | 4/1998 | Stoughton | |
| 5,756,144 A | 5/1998 | Wolff et al. | |
| 5,807,917 A | 9/1998 | Sulc et al. | |
| 5,814,681 A | 9/1998 | Hino et al. | |
| 5,843,086 A | * 12/1998 | Huyser et al. | 606/92 |
| 5,854,469 A | 12/1998 | Gabay | |
| 5,922,227 A | 7/1999 | McMurtrie | |
| 6,004,325 A | 12/1999 | Vargas, III | |
| 6,005,039 A | 12/1999 | Sulc et al. | |
| 6,021,348 A | * 2/2000 | James | 607/3 |
| 6,066,164 A | * 5/2000 | Macher et al. | 607/96 |
| 6,168,571 B1 | 1/2001 | Solar et al. | |
| 6,302,901 B1 | * 10/2001 | Lu | 607/96 |
| 6,334,735 B1 | * 1/2002 | Williams et al. | 404/79 |
| 6,368,339 B1 | 4/2002 | Amplatz | |
| 6,510,346 B2 | * 1/2003 | Gordon | 607/100 |
| 6,563,090 B1 | * 5/2003 | Wu | 219/481 |

FOREIGN PATENT DOCUMENTS

| | | |
|---|---|---|
| JP | 2057230 A2 | 2/1990 |
| WO | WO 9319563 A1 | 9/1993 |

* cited by examiner

Primary Examiner—Teresa Walberg
Assistant Examiner—Vinod D. Patel
(74) Attorney, Agent, or Firm—Luedeka, Neely & Graham, P.C.

(57) ABSTRACT

The present invention is directed toward an improved method and apparatus for securing a prosthesis that is being implanted in a patient. A heat-curable bone cement is used to secure the implanted prosthesis in the patient. A heater is then applied to the prosthesis to decrease the time required for the cement in contact with the prosthesis to cure or set. An adjustable heater control and temperature gauge are used to monitor and control the amount of heat applied to the prosthesis. A socket is provided on the heater such that a tip designed to couple with the particular type of prosthesis being implanted in the patient can be installed on the heater. One or more safety gauges are used to monitor the heater's operation to insure that an excessive amount of heat is not being applied.

21 Claims, 5 Drawing Sheets

APPARATUS AND METHOD FOR PROSTHESIS SECUREMENT

FIELD OF THE INVENTION

The present invention relates generally to surgical attachment of prosthetic devices. More particularly, the present invention relates to the use of a heating device to decrease the curing or setting time of a bone cement used to secure a prosthetic device to a patient.

BACKGROUND OF THE INVENTION

Prostheses are widely used in medicine to replace or supplement various body parts, including joints and limbs. Typically, the prosthesis is attached to the patent during a surgical procedure performed in an operating room. During the surgical procedure, a prosthesis receiving location is prepared in the patient where the prosthesis will be attached. The prosthesis is positioned in the receiving location and a bone cement, such as polymethyl methacrylate cement (PMMA) that binds the prosthesis to the patient's bone, is applied to the prosthesis. The prosthesis is then held in place while the cement cures. This curing time can be relatively long depending upon the type of bone cement used and other factors. Unfortunately, the surgeon and the operating room staff often are required to wait until the cement cures before continuing with the surgery or any other matters they need to tend to. Due to the substantial costs involved in running an operating room, the cost of this down time can be significant. Some bone cement manufacturers have changed the various composite materials used to create the cement in an effort to reduce cure time. Although this approach has been shown to improve upon the cure time of the cement, the change in composition often compromises its ability to adhere to the prosthesis and demonstrate long term clinical stability.

What is needed, therefore, is an improved method and apparatus for securing a prosthesis in a patient.

SUMMARY OF THE INVENTION

The above described deficiencies in the prior art are improved upon by a device for reducing the curing time of a bone cement used to secure a heat-conductive prosthesis inside a patient constructed in accordance with the present invention. The device is a battery powered device that is configured to be hand-held. The device includes a heater for being placed into contact with the prosthesis. The heater has a tip that is designed to couple heat from the heater to the prosthesis. The heater tip produces heat in response to an electrical power signal that is provided to the metal prosthesis through conduction. A power supply generates the electrical power signal and provides the electrical power signal to the heater tip. A trigger activates the power supply to send the electrical power signal to the heater tip when it is depressed. The tip of the heater may be a sterilized heater tip that is designed to be disposed of after each use. In one embodiment, the tip of the heater is removable from the heater and replaceable with a tip from a set of tips wherein each of the tips in the set of tips is configured to mate with a different type of prosthesis. In another embodiment, the heater tip is not removable from the heater. The heater has a temperature gauge that provides an indication of the temperature of the heater tip and an adjustable heater control that allows an operator of the device to select the amount of heat produced by the heater tip.

The present invention is also directed toward a method of securing a metal prosthesis in a patient. The method begins with the securing of the metal prosthesis in a desired position in the patient with a heat-curable bone cement. A heat source is applied to the metal prosthesis such that heat is transferred from the metal prosthesis to the heat-curable cement. The temperature of the applied heat source is monitored to insure that an excessive amount of heat is not applied to the heat-conductive prosthesis. In one embodiment, heat is applied to the metal prosthesis by applying heated air to the surface of the prosthesis. In another embodiment, heat is applied by applying a heated liquid to the metal prosthesis. In yet another embodiment, a heated pad is used to apply heat to the area in which the prosthesis is implanted. Preferably, the heat source is a heater having a heater socket for receiving a sterilized heater tip from a set of sterilized heater tips and a heater tip is installed in the heater socket that is configured to couple with the particular type of metal prosthesis being implanted in the patient. The heat source is then applied to the metal prosthesis for a predetermined amount of time. The heat source is removed from the prosthesis after the cement is sufficiently cured and the used heater tip is discarded.

The above described embodiments provide a number of advantages over the prior art. Most importantly, they reduce the required time for the PMMA cement to cure and, thereby, reduce the time and costs associated with the implantation surgery. The use of disposable sterilized tips allows these advantages to be realized without the need for costly sterilization procedures or the risk of harm to the patient. Furthermore, the provision of a tip socket on the heater allows a heater tip to be selected based upon the particular procedure to be performed. Therefore, the present invention represents a substantial improvement upon the prior art.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

DETAILED DESCRIPTION

Figure 1:
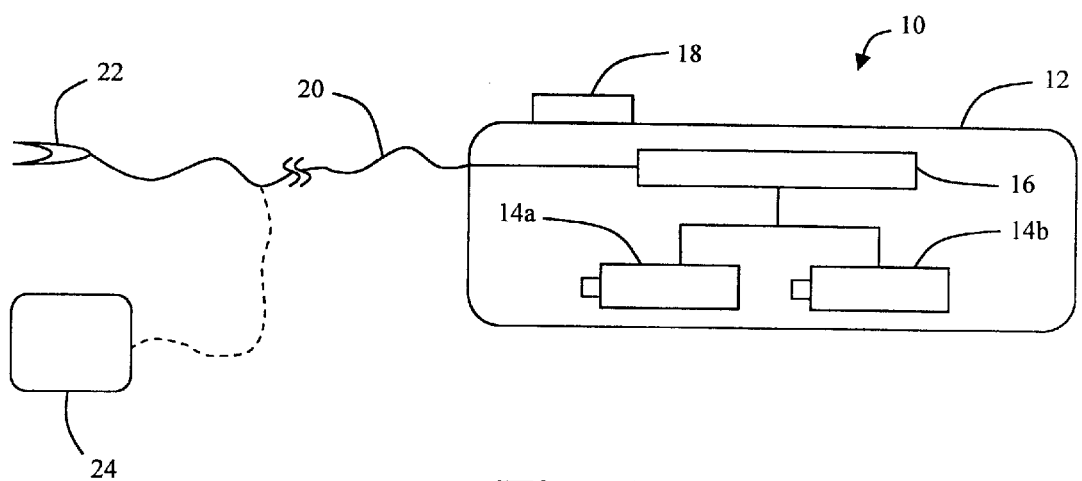
FIG. 1 is a pictorial representation of an embodiment of the present invention.

Referring now to FIG. 1, a pictorial representation of a preferred prosthesis heater 10 constructed in accordance with the present invention is shown. The prosthesis heater 10 includes a housing 12 that encloses a power supply, such as one or more batteries 14a, 14b and an electrical control circuit 16. An activation switch 18 for turning the prosthesis heater 10 on and off is mounted on the housing 12. When the device is activated by switch 18, an electrical line 20 conducts electrical power to a heat transfer mechanism, such as a self-heating clasp 22 or a self-heating pad 24 (shown as an alternate probe by dashed line attachment). The heat transfer mechanism may also take the form of a resistive heating coil. In a preferred embodiment, the heat transfer mechanism 22, pad 24 is readily detachable from line 20 to facilitate its sterilization. Alternatively, the prosthesis heater 10 and its heat transfer mechanism are not detachable from one another but are disposable such that the heater 10 is used once when sterile and then discarded.

In operation, a binding material, such as a heat-curable bone cement known as polymethyl methacrylate cement (PMMA), is applied to a metal or other type of heat conductive prosthesis, and the prosthesis and its applied cement is placed in contact with the patient. The heat transfer mechanism 22, 24 is then placed in contact with the metal prosthesis. When the activation switch 18 is engaged, electrical energy is sent to the heat transfer mechanism 22, 24 and converted to heat energy such that the temperature of the heat transfer mechanism 22, 24 begins to rise. Heat energy from the heat transfer mechanism 22, 24 is then transferred to the metal prosthesis by conduction. This transferred heat causes the temperature of the metal prosthesis to rise which in turn speeds up the curing of the heat curable cement that is in contact with the metal prosthesis. Once the cement has cured, the heat transfer mechanism 22, 24 is removed from the metal prosthesis and the procedure is complete.

The prosthesis heater shown in FIG. 1 decreases the amount of time required to cure the cement that is used to secure the metal prosthesis in the patient. This reduction in curing time reduces the cost associated with the surgery to implant the prosthesis. In addition, heat curing the cement improves the bond between the metal prosthesis and the cement. Thus, the embodiment of FIG. 1 decreases the time and costs associated with the implantation of a metal prosthesis.

Figure 2:
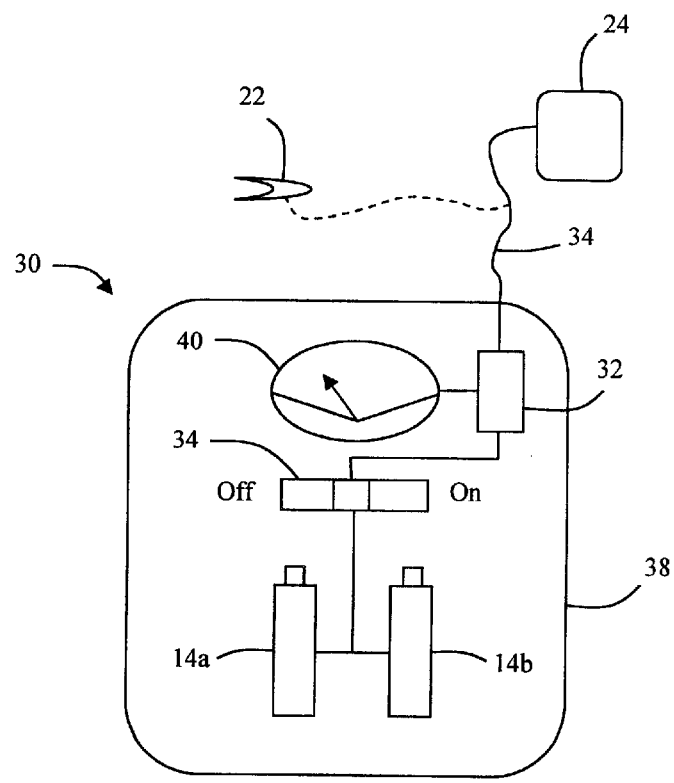
FIG. 2 is a pictorial representation of an embodiment of the present invention having a temperature gauge.

Another embodiment of prosthesis heater 30 is set forth in FIG. 2. Like the embodiment of FIG. 1, the embodiment of FIG. 2 includes control electronics 32 powered by an internal power supply, such as batteries 14a, 14b. The control electronics 32 produce an electrical heating signal that is sent to a heat transfer mechanism, such as a self-heating clasp 22 or a self-heating pad 24, in response to an On/Off switch 34 being placed in the "On" position. The heat transfer mechanism 22, 24 is attached to the device through an electrical cable 36 that is detachable from the housing 38 through the use of a socket or similar mechanism. Thus, if the metal prosthesis is configured such that a pad 24 would be more appropriate for applying heat to the prosthesis, the pad 24 may be plugged into the heater 30 and utilized. Conversely, if a clasp 22 can be easily attached to the neck of the prosthesis, the pad 24 may be replaced with the clasp 22. Heat generated by the clasp 22 is transferred from the neck of the prosthesis to the stem and the cement in contact with prosthesis.

While a clasp 22 and pad 24 are shown, it will be appreciated that a variety of different heat transfer mechanisms can be used with the embodiments shown in FIGS. 1 and 2. In particular, the different types of transfer mechanisms set forth in FIGS. 6A–F and discussed in more detail below could be employed.

With further reference to FIG. 2, a temperature gauge 40 is mounted on the housing 38 to provide a visual indication of the temperature of the installed heat transfer mechanism 22, 24 as sensed by a temperature sensor. The temperature gauge 40 allows medical personnel to monitor the amount of heat being transferred to the metal prosthesis. This is extremely important in certain applications because excessive amounts of heat may damage portions of the patient's bone or other tissue that are in contact with the prosthesis. A timer may also be provided to monitor the length of time in which heat is being transferred to prosthesis.

Figure 3:
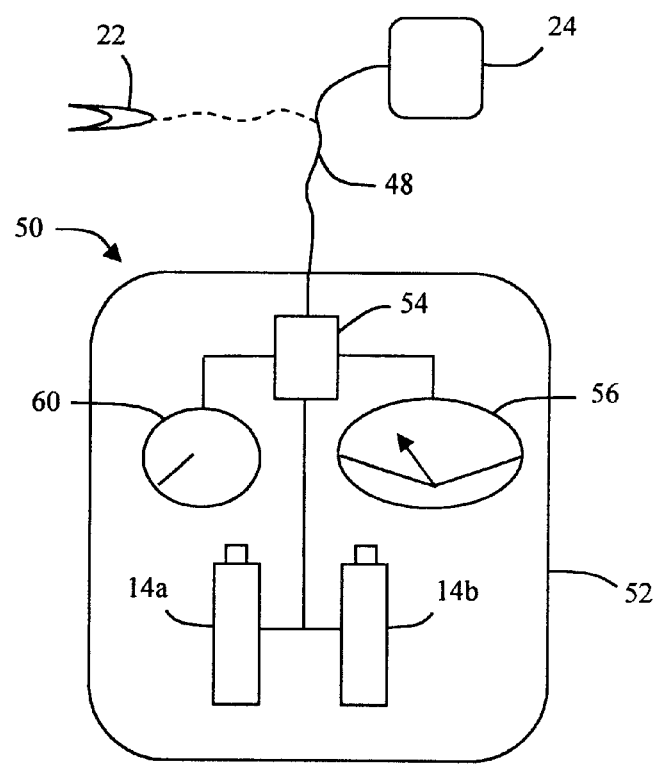
FIG. 3 is a pictorial representation of an embodiment of the present invention having an adjustable heater control.

FIG. 3 discloses yet another embodiment of a prosthesis heater 50. The prosthesis heater 50 includes a housing 52 that contains an internal power supply, such as batteries 14a, 14b, and a microprocessor 54 that respectively power and control the prosthesis heater 50. A temperature gauge 56 displays a reading that is indicative of the temperature of the heat transfer mechanism 22, 24 that is coupled to the prosthesis heater 50 through an electrical connection 58. A heating control 60 is provided to enable a user to adjust the amount of heat produced by the heat transfer mechanism 22, 24 by adjusting the amount of power supplied to the heat transfer mechanism 22, 24. Alternatively, the temperature gauge 56 may be replaced by, or supplemented with, a power gauge that displays a signal indicative of the amount of power being supplied to the heat transfer mechanism 22, 24.

Figure 4:
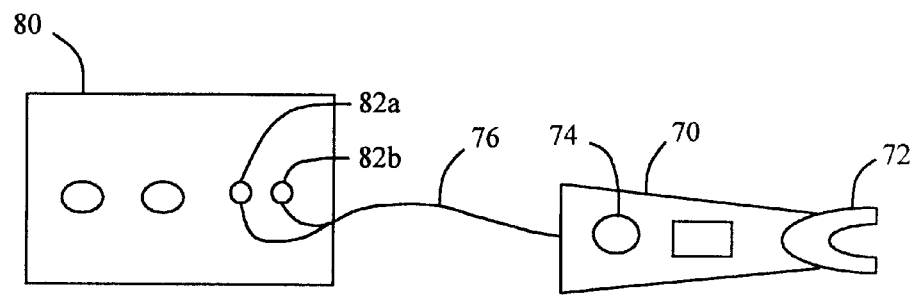
FIG. 4 is a pictorial representation of an embodiment of the present invention for use in conjunction with pre-existing hospital equipment.

FIG. 4 discloses an embodiment of a prosthesis heater 70 that is designed to work with preexisting medical equipment. The prosthesis heater 70 includes a specially configured heater tip 72 designed for mating with a metal prosthesis and a power control 74 that enables a user to control the amount of power supplied to the heater tip 72. Line 76, which may include one or more lines, in one embodiment electrically couples the prosthesis heater 70 to power supply 80 through a set of connection ports 82a, 82b. In this embodiment, power supply 80 is a readily available electrical power supply commonly used in the medical industry that provides an electrical signal to power the prosthesis heater 70 through line 76. Alternatively, power supply 80 functions as a direct heat supply source that heats a medium, such as air or water, and then forces the heated medium by way of line 76 to the prosthesis heater 70. In this embodiment, line 76 is a set of flexible tubes capable of conducting the heated medium to and from the heater 70. Heated air may be applied directly to the cement/implant interface with heater tip 72 or indirectly to a sterile covering placed over the area to be heated. The use of preexisting medical equipment to power the prosthesis heater 70 reduces the costs associated with its use. In addition, as discussed in more detail below, it facilitates the advantageous use of disposable sterile prosthesis heater tips 72 which are preferably made from or coated with a material that inhibits the tip 72 from scratching or otherwise marring the prosthesis.

Figure 5:
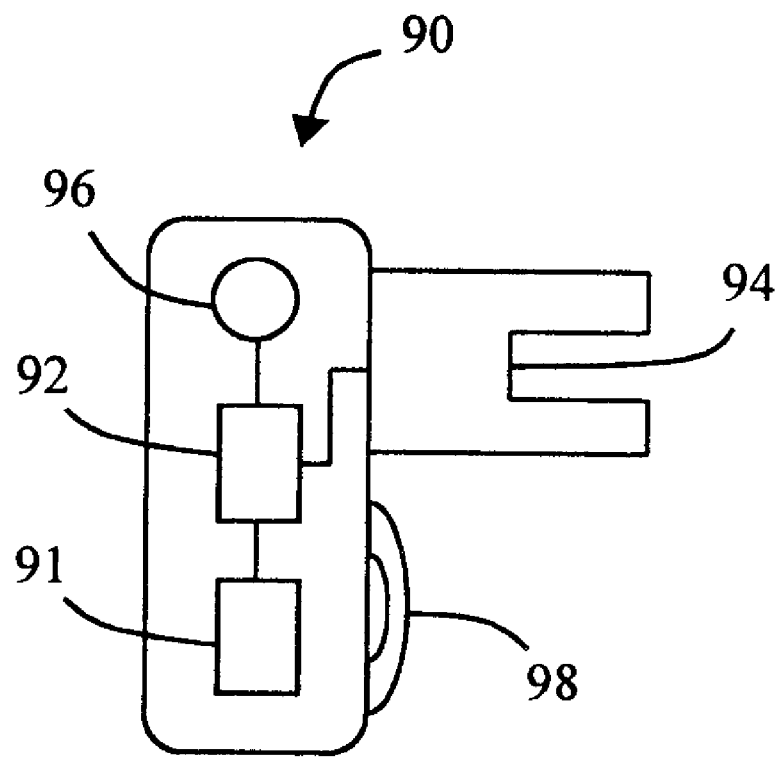
FIG. 5 is a pictorial representation of an embodiment of the present invention that utilizes interchangeable tips.

FIG. 5 depicts an embodiment of a prosthesis heater 90 that utilizes interchangeable heating tips. The hand-held prosthesis heater 90 includes a power source 91, which is preferably internal to the heater 90, providing power to control electronics 92 that send an electrical power signal to a heater tip 100–110 (FIGS. 6A–F) that is detachably mounted in a socket 94. The amount of power sent to the tip installed in the socket 100 is adjustably controlled with a dial 96 or other suitable user interface mounted on the heater 90. In addition, the control electronics 92 may include a temperature regulator that enhances safety by cutting power to the heater tip if a maximum allowable temperature level is exceeded. A trigger 98 is provided to enable quick, non-contact release of the tip 100–110. The trigger 98 is particularly useful for releasing hot tips since it allows the tip to be released without being touched or otherwise contacted by the user.

Figure 6A:
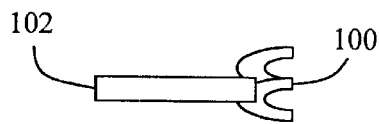
FIGS. 6A–F show various interchangeable tip configurations for utilization with the embodiment of FIG. 5.
Figure 6B:
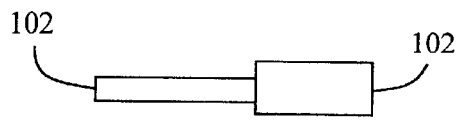
Figure 6C:
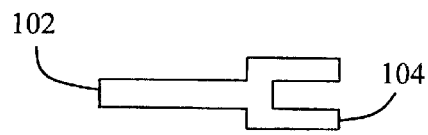
Figure 6D:
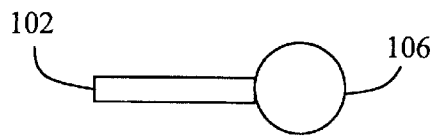
Figure 6E:
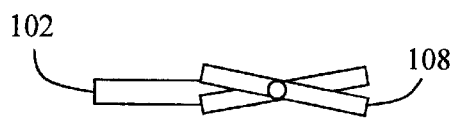
Figure 6F:
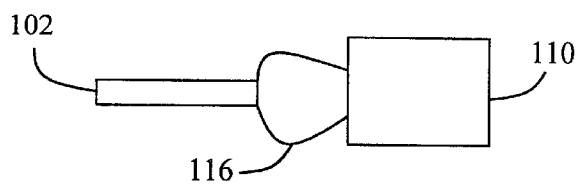

Each heater tip 100, 102, 104, 106, 108 and 110 of FIGS. 6A–F includes a projection 102 that is received at socket 94. The tips 100–110 are preferably constructed out of a non-corrosive material such as a heat tolerant plastic or a graphite composite that will not scratch the metal prosthesis. Each tip 100–110 is designed to mate with a particular type of prosthesis that may need to be heated. For example, tip 100 of FIG. 6A includes a relatively large surface area that is useful with a femoral prosthesis in the knee, which tip 102 of FIG. 6B is configured for use with a tibial prosthesis. Tips 104, 106 and 108 are particularly useful in conjunction with hip and shoulder prostheses. Tip 110 includes a pad that is flexibly connected to the mating portion 102 by a set of electrical cables 1 12.

It will be appreciated that the tips 100–110 of FIGS. 6A–F are exemplary only and a large number of additional types of tips could be used in accordance with the invention. In most situations, the particular tip used will be dependent upon the type of procedure to be performed and the type of prosthesis to be heated.

Heating the metal prosthesis to decrease the curing time required for the cement to set is beneficial in a number of respects. First, the reduction in the curing time reduces the time required to perform the procedure. This in turn reduces the cost of the procedure and the trauma to the patient on whom the procedure is being performed. In addition, the manner in which the heat is conducted through the metal prosthesis allows the heat to reach portions of the cement that are not exposed to the surgeon and easily reached.

Figure 7:
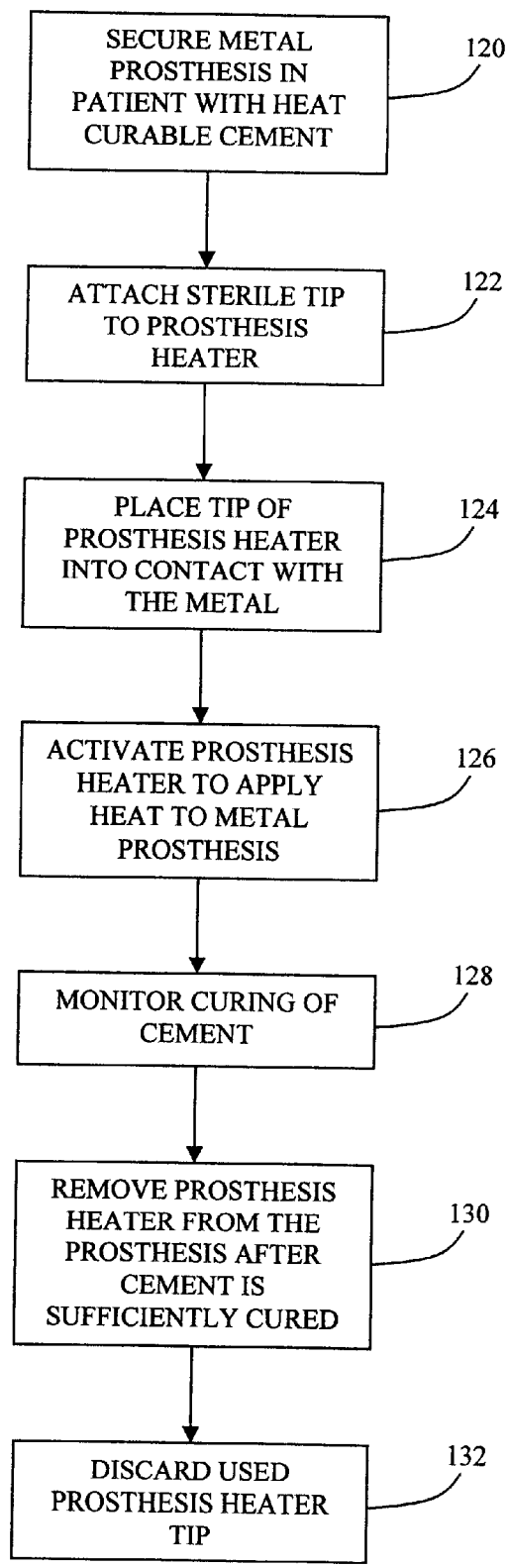
FIG. 7 is a flow chart showing a preferred method of securing an implanted prosthesis in accordance with the present invention.

FIG. 7 illustrates a preferred method of curing the cement used to attach a metal prosthesis into a patient's body in accordance with the present invention. The method commences with the securing of a metal prosthesis inside of a patient with a heat-curable cement as shown in block 120. A sterile tip is attached to the prosthesis heater in block 122. Once the sterile tip is attached, the tip of the prosthesis is placed into contact with the metal prosthesis in block 124. In block 126, the prosthesis heater is activated to apply heat to the metal prosthesis. Due to the conductive nature of metal, the heat applied to the metal prosthesis is conducted through the prosthesis to the heat-curable cement that is in contact with the prosthesis. This heat decreases the time required for the heat-curable cement to set or cure. In block 128, the curing of the cement is monitored. The curing may be monitored directly by the medical personnel performing the procedure or according to a predetermined criteria such as the passage of a certain amount of time. Once the cement is sufficiently cured, the prosthesis heater is removed from the prosthesis in step 130. Finally, the used prosthesis heater tip is discarded in 132. Using a disposable sterile heater tip is beneficial in that it eliminates the need to sterilize the tip prior to each procedure while preventing the spreading of germs during the procedure.

In view of the above explanation of the particular features of the present invention, it will be readily appreciated by one skilled in the art that the present invention can be usefully employed in a wide variety of embodiments. While certain embodiments have been disclosed and discussed above, the embodiments are intended to be exemplary only and not limiting of the present invention. The appropriate scope of the invention is defined by the claims set forth below.

What is claimed is:

1. An apparatus for reducing the curing time of a bone cement used to attach a heat conductive prosthesis to a patient, said apparatus comprising:

a heat generating element for being placed adjacent the prosthesis; and a prosthesis heater for providing energy to heat the heat generating element while the heat generating element is adjacent the prosthesis;

wherein a sufficient amount of heat is transferred from the heat generating element to the prosthesis to reduce the curing time of a cement that is in contact with the prosthesis.

2. The apparatus of claim 1 wherein said heater includes a temperature gauge to provide a visual indication of the temperature of the heat generating element.

3. The apparatus of claim 1 wherein said heat generating element is detachably connected to the heater.

4. The apparatus of claim 3 wherein said heater includes a trigger for non-contact release of the heat generating element from the heater.

5. The apparatus of claim 1 wherein said heater includes a control circuit for controlling operation of the apparatus.

6. The apparatus of claim 1 wherein said heater includes an adjustable heater control that allows an operator of the apparatus to select the amount of heat produced by the heat generating element.

7. The apparatus of claim 1 wherein said heat generating element is sterilized and disposable.

8. The apparatus of claim 1 wherein said heat generating element is a clasp.

9. The apparatus of claim 1 wherein said heat generating element is a pad.

10. The apparatus of claim 1 wherein said apparatus is battery powered.

11. An apparatus for reducing the curing time of a bone cement used to attach a heat conductive prosthesis to a patient, said apparatus comprising:

a heat generating element for being placed adjacent the prosthesis; and a prosthesis heater for providing energy to heat the heat generating element while the heat generating element is adjacent the prosthesis, said heater including:

a power supply for supplying electrical power to operate the apparatus;

a control circuit for controlling operation of the apparatus; and a temperature gauge for providing a visual indication of the temperature of the heat generating element;

wherein a sufficient amount of heat is transferred from the heat generating element to the prosthesis to reduce the curing time of a cement that is in contact with the prosthesis.

12. The apparatus of claim 11 wherein said heat generating element is detachably connected to the heater.

13. The apparatus of claim 12 wherein said heater includes a trigger for non-contact release of the heat generating element from the heater.

14. The apparatus of claim 11 wherein said heater includes an adjustable heater control that allows an operator of the apparatus to select the amount of heat produced by the heat generating element.

15. The apparatus of claim 11 wherein said heat generating element is sterilized and disposable.

16. The apparatus of claim 11 wherein said heat generating element is a clasp.

17. The apparatus of claim 11 wherein said heat generating element is a pad.

18. The apparatus of claim 11 wherein said apparatus is battery powered.

19. A method of securing a metal prosthesis in a patient, said method comprising:

applying a heat-curable bone cement to the prosthesis;

positioning the prosthesis and the applied cement in contact with the patient; and applying a heat source to the metal prosthesis such that heat is transferred from the metal prosthesis to the heat-curable cement to speed the curing time of the cement.

20. The method of claim 19 wherein the step of applying a heat source further comprises placing a heat generating element in contact with the metal prosthesis.

21. The method of claim 19, further comprising monitoring the temperature of the applied heat source to insure that an excessive amount of heat is not applied to the heat-conductive prosthesis.

* * * * *